United States Patent [19]

Shetty

[11] Patent Number: 5,221,693
[45] Date of Patent: Jun. 22, 1993

[54] ANTIMICROBIAL AND ANTIVIRAL BIS-ADAMANTANAMINE COMPOUNDS

[75] Inventor: B. Vithal Shetty, Rockville, Md.

[73] Assignee: The United States of America as represented by the Secretary of the Department of Health & Human Services, Washington, D.C.

[21] Appl. No.: 888,438

[22] Filed: May 28, 1992

Related U.S. Application Data

[63] Continuation of Ser. No. 571,910, Aug. 24, 1990, abandoned.

[51] Int. Cl.$^5$ ................................................ A61K 1/22
[52] U.S. Cl. ............................... 514/635; 564/233; 564/235
[58] Field of Search ................. 564/233, 235; 514/635

[56] References Cited

U.S. PATENT DOCUMENTS

| | | | |
|---|---|---|---|
| Re. 32,300 | 12/1986 | Gorman et al. | 514/635 |
| 3,270,036 | 8/1966 | Bernstein et al. | 564/233 |
| 3,468,898 | 9/1969 | Cutler et al. | 564/233 |
| 4,022,834 | 5/1977 | Gundersen | 564/233 |
| 4,100,170 | 7/1978 | Shetty | 514/635 |
| 4,954,636 | 9/1990 | Merianos et al. | 564/233 |

FOREIGN PATENT DOCUMENTS

| | | | |
|---|---|---|---|
| 126558 | 4/1984 | European Pat. Off. | 564/233 |
| 125092 | 11/1984 | European Pat. Off. | 564/233 |

OTHER PUBLICATIONS

Windholz et al, The Merck Index 9th ed. (1976) cpd. 377 and 9434.
Aldrich–Catalogue, Aldrich Chemical Company, 940 W. St. Paul Ave. Milwaukee, Wis. 53233 and computer search by Aldrich.
Derwent Publications Ltd.; Abstract of EP-126-55-8-A; "New alkane-bis:substd.-biguanide(s)"; 1984.

*Primary Examiner*—James H. Reamer
*Attorney, Agent, or Firm*—Birch, Stewart, Kolasch & Birch

[57] ABSTRACT

Several bis-adamantanamine compounds have been found to have a broad range of antiviral and antibacterial activities. Demonstrated activity against enveloped viruses, yeasts, fungi, gram positive and gram negative bacteria is shown.

26 Claims, No Drawings

ANTIMICROBIAL AND ANTIVIRAL BIS-ADAMANTANAMINE COMPOUNDS

This application is a continuation of application Ser. No. 07/571,910, filed on Aug. 24, 1990, now abandoned.

BACKGROUND OF THE INVENTION

Amantadine is a well known anti-viral agent which has been commercially available for years under the brand name Symmetrel. Its primary use is for preventing influenza A infections though higher doses (25-50 $\mu g/ml$) can inhibit other viruses as well (Hayden et al, Principles and Practice of Infectious Diseases, 2nd ed. Wiley, N.Y. (1985) p. 270-286). Its mode of action is thought to be at an early stage in replication probably at the state of uncoating. Attachment and penetration of the virus to a cell is not affected by amantadine (Skehel et al, J. Gen. Virol. 38 p. 97-110 (1978).

SUMMARY OF THE INVENTION

The present invention relates to a new class of compounds containing both polar and non-polar regions. The basic structure is somewhat symmetrical in the broadest sense but not strictly so and is represented below:

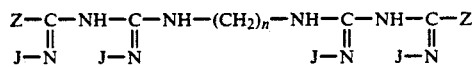

or

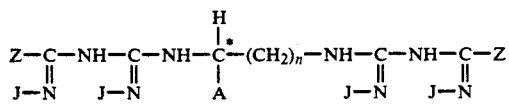

where A is a hydrogen, straight or branched chain alkane of 1-6 carbon atoms and * may be an optically active carbon
where the A substituted carbon may be any of the central carbon atoms between the two guanido moieties

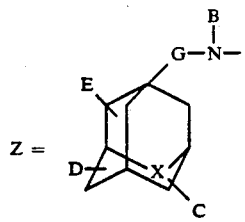

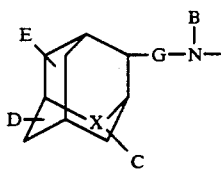

where B is hydrogen, lower alkyl, halogen substituted lower alkyl, hydroxyalkyl,
where G is zero, lower alkyl, or —NH—
where C, D, and E, individually are hydrogen, amino, substituted amino, alkyl, preferably lower alkyl, halogen substituted lower alkyl, aminoalkyl, phenyl, phenalkyl, halogen, haloadamantyl, pyridyl, or

where B1 and B2 are hydrogen, phenyl, phenylalkyl, COOD1, COD1, or —OD1, and D1 is hydrogen, alkyl, preferably lower alkyl or substituted alkyl.
where each J is hydrogen or halogen with any number from zero to four halogens or hydrogens being present.
X is carbon, nitrogen, oxygen or sulfur. and wherein n is an integer from 2 to 30 carbon atoms wherein the polymethylene chain may contain side chains or be interrupted by one or more oxygen, sulfur, nitrogen atoms, silicone, aromatic nuclei, or combination of these.

These compounds are broadly antibiotic and antiinfective and have a wide range of uses in therapy as a medicinal agent for human or veterinary uses, as antiseptic to be applied to any surface including body parts, disinfectant for contaminated surfaces used either alone or with a surfactant to aid in cleaning, as growth promotor when used in animal feeds, as a preservative in food or degradable chemicals or products and as an antimicrobial agent to contact fluids. In particular, these compounds are biologically active against gram positive and gram negative bacteria, fungi, yeasts and enveloped viruses, especially enveloped viruses such as herpes viruses and retroviruses (HIV etc.).

PREFERRED EMBODIMENT

The particular compounds discovered to have antimicrobial activity have the general structures illustrated below:

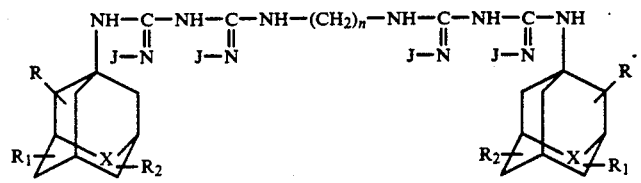

or

-continued

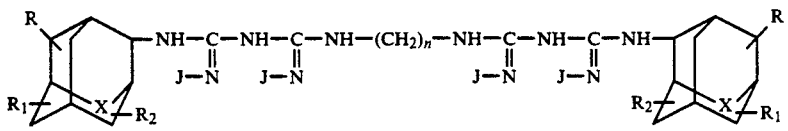

wherein X is carbon, nitrogen, oxygen or sulfur,
wherein n is an integer from 2 to 30,
wherein R, R1 and R2 are hydrogen, halogen, alkyl, phenyl, phenylalkyl, aminoalkyl, haloadamantyl, pyridyl, —COOR3, —COR3, —OR3, —NR4 where R3 and R4 are hydrogen alkyl, phenyl or phenylalkyl.
where each J is hydrogen or halogen with any number from zero to four halogens or hydrogens being present.

The polymethylene chain may be interrupted by one or more oxygen, sulfur, nitrogen atoms, silicone, aromatic nuclei or combination of these.

The optically active carbon may exist by having a lower alkyl instead of a hydrogen in any of the central carbon atoms between the two guanido moieties, $(CH_2)_n$ region. The location of the optically active carbon is not important as any will enable the compound to be resolved into dextro and levorotary forms. The compound may remain and be used as a racemic mixture as well.

Representative examples of the above class of compounds include the dihydrochloride or salts of:
1,5-di(N-3-methyl adamantyl-biguanido)-pentane
1,6-di(N-3-methyl adamantyl-biguanido)-hexane
1,3-di(N-adamantyl biguanido)-propane
1,2-di(N-adamantyl biguanido)-ethane
1,8-di(N-adamantyl biguanido)-octane
1,8-di(N-3-methyl adamantyl biguanido)-octane
1,9-di(N-adamantyl biguanido)-nonane
1,10-di(N-adamantyl biguanido)-decane
1,11-di(N-adamantyl biguanido)-undecane
1,5-di(N-adamantyl biguanido)-2-methyl pentane
1,6-di(N-3-methyl adamantyl biguanido)-2-methyl pentane
1,12-di(N-adamantyl biguanido)-dodecane
1,13-di(N-adamantyl biguanido)-tridecane
1,6-di(N-adamantyl-N-chloro-biguanido)-hexane
1,6-di(N-adamantyl-N,N'-dichloro-biguanido)-hexane
1,6-di(N-adamantyl-N,N',N''-trichloro-biguanido)-hexane
1,6-di(N-adamantyl-N,N',N'',N'''-tetrachloro-biguanido)-hexane
1,14-di(N-adamantyl biguanido)-tetradecane
1,5-di(N-adamantyl biguanido)-pentane
1,4-di(N-2-adamantyl biguanido)-butane
1,6-di(N-2-adamantyl-N-chloro-biguanido)-hexane
1,6-di(N-2-adamantyl-N,N'-dichloro-biguanido)-hexane
1,6-di(N-2-adamantyl-N,N',N''-trichloro-biguanido)-hexane
1,6-di(N-2-adamantyl-N,N',N'',N'''-tetrachloro-biguanido)-hexane
1,3-di(N-2-adamantyl-biguanido)-propane
1,2-di(N-2-adamantyl-biguanido)-ethane
1,8-di(N-2-adamantyl-biguanido)-octane
1,9-di(N-2-adamantyl-biguanido)-nonane
1,10-di(N-2-adamantyl-biguanido)-decane
1,11-di(N-2-adamantyl-biguanido)-undecane
1,12-di(N-2-adamantyl-biguanido)-dodeoane
1,13-di(N-2-adamantyl-biguanido)-tridecane
1,6-di(N-2-adamantyl-biguanido)-2-methylpentane Obviously, this list is merely representative of the various compounds encompassed by the general formula presented above and should not be considered as an exhaustive list of compounds. These compounds can be made following the general synthesize methods taught herein and one skilled in the art will readily understand the modifications and components needed to synthesize all of the compounds.

The exact mechanism of how the novel compounds operate is unknown for most microorganisms. While parts of some of these molecules resemble the known antiviral compound amantadine applicant does not wish to be bound by any particular theory. For the compounds' antiviral effect, they may interact with or through the membrane as enveloped viruses are affected by these compounds much more than non-enveloped viruses as will be shown by the data below. This is different from the mechanism by which amantadine is thought to operate. In any case, the mode of action has not been established and therefore applicant should not be bound by such a theory especially with respect to his compounds.

It is a further object of this invention that these compounds can be used to prevent an infection from becoming established as well as treatment after infection. Examples of such preventative use may be for people potentially exposed to an infectious agent but are uncertain whether or not they are actually infected such as when one has been injured or exposed to known contaminated objects or contacted contaminated fluids. Other suitable times to provide therapy is during an outbreak or epidemic of an infectious disease or when a subject is immunocompromised due to genetic, environmental, therapeutic or other preexisting conditions.

One interesting property of these compounds is that at least some have a multiple separate actions or are bifunctional in their mode of action. For example, both antibacterial and antiviral activity may be possessed in the same compound. This dual action is a particularly desirable property in patients who are immunosuppressed as they frequently have difficulty with plural infections. Patients with AIDS are well known to be susceptible to many opportunistic infections which may be treated or prevented simultaneously with providing antiviral therapy. Bifunctional activity is also particularly desirable between antibacterial and antiyeast activities as certain conventional antibacterial agents such as the tetracyclines frequently cause vaginal Candida albicans infections. Still other advantages of bifunctional activities are readily apparent when using the compounds and compositions of the invention as wide spectrum disinfectants, antibiotics in cell, tissue or organ culture or preservative mediums or as a growth promotor which may simultaneously treat or prevent an animal infection.

The range of antibiotic activity may vary depending on the particular compound being used. While antibacterial, antiviral and antifungal activities are most pronounced, antiprotozoan, antiparasitic, antineoplastic and a variety of metabolic changes may be noticed.

The compounds of the invention used alone or in combination with each other or with other antibiotic compounds not of this invention. These compounds and compositions would typically be used with a pharmaceutically acceptable carrier to facilitate administration of the active ingredient. Also esters of the described compounds may also be used. The particular formulation is not critical.

Examples of physiologically or pharmaceutically acceptable salts of the compounds or acceptable derivatives thereof include base salts, e.g. derived from an appropriate base, such as alkali metal, alkaline earth metal salts, ammonium, and $NX_4$ wherein each X is hydrogen or an alkyl with 1-4 carbon atoms. Acceptable salts containing a hydrogen atom or an amino group include salts of organic carboxylic acids such as acetic, lactic, tartaric, glucuronic, malic, succinic: organic sulfonic acids such as methanesulfonic, ethanesulfonic, benzenesulphonic; and inorganic acids such as hydrochloric, sulfuric, phosphoric, sulfamic acids. Acceptable salts of a compound containing any hydroxy group include the anion of said compound in combination with a suitable cation such as sodium, $NX_4$, $NHX_3$, $NH_2X_2$, $NH_3X$ wherein X is alkyl having 1-4 carbon atoms.

Also included within the scope of this invention are the pharmaceutically acceptable salts, esters, salts of such esters, nitrile, oxides, or any other covalent linked or non-linked compounds which upon administration to the individual or material being treated, is capable of providing (directly or indirectly) the compound described in the invention or a biologically active metabolite thereof. All of these compounds are active and relatively non-toxic at concentrations sufficient for effective inhibition or killing of the microorganism.

It is possible for the compounds of the present invention to be administered alone in solution. However, in the preferred embodiment, the active ingredient(s) may be used or administered in a pharmaceutical formulation. These formulations comprise at least one active ingredient, together with one or more pharmaceutically acceptable carriers and possibly other active or inactive therapeutic ingredients. As included within the scope of the invention, "acceptable" is defined as being compatible with other ingredients of the formulation and relatively non-injurious to the patient or material being treated. These carriers include those well known to practitioners in the art as suitable for oral, rectal, nasal, topical, buccal, sublingual, vaginal, transdermal, subcutaneous, intradermal, intramuscular, intravenous, intrathecally or other parenteral administration. Specific carriers suitable for use in the invention are further defined below.

In general, a suitable dose in humans is in the range of about 5 mg to about 500 mg per day although higher and lower amounts may be used depending on the severity of the infection, the means of administration and the weight of the person. For veterinary uses, the dosage would be correspondingly based upon the animal species and size being treated. The desired dose is preferably provided in several increments at regular intervals throughout the day or by continuous infusion or sustained release formulations. The doses will need to be modified according to the type of material being treated, the species of the patient, the particular infectious agent one wishes to treat or prevent, the condition of the patient, and the nature of whatever other treatment is being employed.

The antimicrobial compounds of the invention may be administered orally in liquid or in solid form and may include any of the following: antacids, lactose (hydrous, fast flow etc.), microcrystalline cellulose, colloidal silicon dioxide, magnesium stearate, stearic acid and other excipients, binders, colorants and other pharmacologically compatible carriers. Compositions for oral use may be administered to patients in fasting or non-fasting states.

Formulations of the present invention suitable for oral administration include sustained release formulations and may be presented in discrete units such as capsules, cachets, or tablets each containing a predetermined amount of the active ingredient(s). The shape and form of the solid are immaterial and it may be composed of smaller solids such as powders or granules. The formulation may be in liquid form such as a solution, suspension, oil-in-water or water-in-oil emulsion. Other acceptable formulations include a bolus, electuary or paste.

The oral dose may optionally be provided with an enteric coating to provide release in any part of the digestive track so desired.

Formulations suitable for topical administration in the mouth include lozenges comprising the active ingredient with an acceptable flavorant such as sucrose and acacia or tragacanth; with an inert ingredient(s) such as gelatin or glycerin; or a combination of both. Mouthwash comprising the active ingredient and a liquid carrier are also acceptable in accordance with the invention.

Formulations for topical and transdermal administration include a suitable carrier such as a cream or base of other material to facilitate contact with the skin or mucus membranes. The active ingredient(s) contained therein may be charged, or converted into a salt in order to permit crossing the surface under the influence of an electrical field. Alternatively, the active ingredient may be derivatized in order to enhance absorption or transport across the cell layer.

Formulations for rectal administration may be presented as a suppository with a suitable base, for example, comprising cocoa butter or a salicylate.

Formulations suitable for vaginal administration may be presented as pessaries, tampons, creams, gels, pastes, foams or spray formulas containing such carriers as are known in the art to be appropriate in addition to the active ingredient(s).

Formulations suitable for parenteral administration include aqueous and non-aqueous, isotonic and isosmotic sterile injection solutions which may contain antioxidants, buffers, bacteriostats, and solutes which render the formulation isotonic with the body fluids of the intended recipient and aqueous and non-aqueous sterile suspensions which may include suspending agents and thickening agents. The formulations may be presented in unit-dose or multi-dose sealed containers, such as ampules and vials, and may be stored in a freeze-dried (lyophilized) condition requiring only the addition of the sterile liquid carrier (e.g. water, saline) for injection immediately prior to use. Extemporaneous injection solutions and suspensions may be prepared from powders, granules and tablets of the kind previously described. In all cases, the final product is preferably free of pyrogens.

For long term therapy, oral administration is highly desirable. Since some of the compounds of the invention may not be stable in the acid range it may be necessary to buffer or otherwise protect the composition in the neutral range to provide adequate bioavailability.

The compounds of the invention may be used topically as disinfectants, antiinfectives or to remove, inactivate or kill organisms in solution. The compounds may also be applied to or in food or animal feed to preserve it or as a growth promoting agent. Biodegradable products (cosmetics, sensitive chemicals, etc.) may also be coated with or incorporate one or more of the compounds to prevent microbial degradation or to extend shelf life. Uses in solution include as a preservative (for food or chemicals), in water (or other liquid) to kill existing microorganisms, or in fish tanks, swimming pools and the like to reduce microorganism populations. The uses include a variety of medical, industrial, food/feed, chemical and personal product uses.

The antibiotic compounds of the invention may be used in conjunction with other drugs, other antibiotics or immunomodulating chemicals. Other forms of therapy such as non-chemical therapy may also be concurrently used. When not used therapeutically, the compounds may be used alone or with a variety of carriers or dispersants. Alternatively, these compounds may be bound to a solid phase as a surface coating or particulate for performing the same function.

EXAMPLE 1

The compound 1,6-di(N-2-adamantyl-biguanido)-hexane dihydrochloride was synthesized in the following manner. To a 500 ml round bottomed flask equipped with a condenser and a magnetic stirrer, 10.24 g. (0.05 mole) of 2-adamantanamine hydrochloride, 5.32 g. (0.022 mole) of 1,6-hexamethylene-bisdicyandiamidine and 100 ml of n-butanol were added and mixed. The mixture was heated in an oil bath and refluxed with stirring for 52 hours. The resulting white solid was removed by filtration while the solution was hot. It was air dried to yield 6.7 g. The solid was recrystallized by dissolving in a mixture of 300 ml of absolute ethanol and 50 ml absolute methanol, adding Norit A (activated charcoal), filtering and partially precipitating with anhydrous ether to yield 4 grams. The melting point of the recrystallized solid was 270°-272° C. The calculated percentage analysis for $C_{30}H_{54}N_{10}Cl_2$ is C-57.58, H-8.69, N-22.38, Cl-11.33. The experimental percentage analysis was C-57.33, H-8.88, N-22.25, Cl-11.21.

EXAMPLE 2

The compound 1,6-di(N-adamantyl-biguanido)-hexane dihydrochloride was synthesized in the following manner. To a 500 ml one-necked round bottomed flask equipped with a condenser and a magnetic stirrer, 20.58 g. of 1-adamantanamine hydrochloride, 10.64 g. of 1,6-hexamethylene-bis-dicyandiamidine (III) and 200 ml of n-butanol were added. The mixture was heated to reflux with stirring for 43 hours. The clear solution was filtered while hot and allowed to stand at room temperature for one week. The solvent was removed under vacuum and heat. It formed a thick semi-solid. It was washed with anhydrous ether, dissolved in 150 ml absolute methanol, digested with Norit A (activated charcoal) and filtered. It was concentrated to about 50 ml, mixed with about 50 ml acetyl nitrile, filtered and the solvent was removed in vacuum. The resulting product was dissolved in absolute ethanol and precipitated with acetone. The resulting solid was dried. It had a melting point of 260° to 265° C. The calculated percentage analysis for $C_{30}H_{54}N_{10}Cl_2$ is C-57.58, H-8.69, N-22.38, Cl-11.33. The experimental percentage analysis was C-56.38, H-8.64, N-22,71, Cl-11.20.

EXAMPLE 3

The compounds produced in examples 1 and 2 were tested against a panel of microorganisms to determine the minimal inhibitory concentration.

To the first well of a test plate 1 ml of the compound in solution of examples 1 or 2 was added. To each adjacent well, 0.5 ml of Mueller-Hinton broth supplemented with calcium and magnesium ions was added. 0.5 ml of the compound in solution was added to the adjacent well to make a 1:1 dilution. The process was repeated making two fold dilutions until the end of the plate of wells and from the last 0.5 ml was discarded.

The inoculum of each microorganism was grown out in Mueller-Hinton Broth. The inoculum was then diluted to $10e^5$–$10e^6$ microbes against a McFarland standard for turbidity. 0.5 ml of inoculum was added to each test well of the test plates and one normal growth control was added. The test plates were incubated for 16–20 hours at 35° C. and examined for growth. The lowest concentration of antimicrobial agent that completely inhibits visible growth represents the minimal inhibitory concentration (MIC).

For fungal growth and testing a similar system was used. To the first well of a test plate 1 ml of the compound of examples 1 or 2 in solution at 128 µg/ml was added. To each adjacent well, 0.5 ml of Yeast Nitrogen Broth was added. 0.5 ml of the compound in solution was added to the adjacent well to make a 1:1 dilution. The process was repeated making two fold dilutions until the end of the plate of wells and from the last 0.5 ml was discarded.

The inoculum of each microorganism was grown out in Yeast Nitrogen Broth. The inoculum was then diluted to McFarland #1 standard for turbidity. 0.05 ml of inoculum was added to each test well of the test plates and one normal growth control was added. The test plates were incubated for 48 hours or until the growth control was grew out. The lowest concentration of antimicrobial agent that completely inhibits visible growth represents the minimal inhibitory concentration.

RESULTS

Following the standard methods listed above, the minimal inhibitory concentration for the compounds of examples 1 and 2 against the particularly broad range of microorganisms listed are given below.

| 1,6-di(N-2-adamantyl-biguanido)-hexane dihydrochloride (BVS 48B) | |
|---|---|
| *Pseudomonas aeruginosa* ATCC 27853 | 32 µg/ml |
| *Escherichia coli* ATCC 25922 | 16 µg/ml |
| *Staphylococcus aureus* ATCC 29213 | 2 µg/ml |
| *Candida albicans* ATCC 10231 | 8 µg/ml |
| *Aspergillus niger* ATCC 10535 | <4 µg/ml |
| 1,6-di(N-adamantyl-biguanido)-hexane dihydrochloride (BVS 54C) | |
| *Pseudomonas aeruginosa* ATCC 27853 | 32 µg/ml |
| *Escherichia coli* ATCC 25922 | 2 µg/ml |
| *Staphylococcus aureus* ATCC 29213 | 8 µg/ml |
| *Candida albicans* ATCC 10231 | <0.25 µg/ml |
| *Aspergillus niger* ATCC 10535 | <4 µg/ml |

EXAMPLE 4

Unlike most microorganisms, viruses are obligate intracellular parasites which are essentially inert outside a host cell and utilize the cellular metabolism in their lifecycle. These properties make them fundamentally different from other microorganisms and present additional problems in inhibiting their growth. For example, destroying the cellular metabolism may inhibit viral growth but also inhibits that which one wishes to preserve.

The ability of the test compounds to block viral growth in cells was determined as follows. BGM cells were exposed to various concentrations of the compounds of example 1 and 2. Following 24 hours of incubation at 37° C., the cells were washed twice and challenged with a number of concentrations of Poliovirus I or Coxsackie B5a and incubated at 37° C. for 96 hours The compounds were toxic to BGM cells at 10, 25, 50 and 100 μg/ml. At concentrations of 1 and 5 μg/ml, the compounds of examples 1 and 2 failed to protect the cells.

The virucidal activity of the compounds were tested by a second standard method. The U.S. Environmental Protection Agency method, 1976, DIS/TSS-7 Nov. 12, 1981 was used for this test with the following exceptions: the virus used was fresh and not dried on a surface and the compound was not neutralized. 0.5 ml aliquots of stock suspensions of Poliovirus I (Brunhilde-VR-ATCC-58) and Coxsackie B5a (NIAID-V032) having an infectivity titer of $10^{7.5}$ TCID$_{50}$/ml each were added to test tubes containing a series of solutions with concentrations of the compounds of examples 1 and 2 ranging from 0.1 μg/ml to 100 μg/ml. The mixtures were incubated for one hour at room temperature. At the end of this period, the contents of each tube were assayed for infectious virus and or cytotoxicity. Seven serial 10-fold dilutions of each mixture were made and duplicate 1 ml aliquots were plated on fresh monolayers of BGM cells in 24-well plates. The virus control comprised of stock virus suspensions and maintenance medium. The BVS cytotoxicity controls comprised maintenance medium only. The controls for this test consisted of toxicity control, virus control and cell control. Toxicity control solution was comprised of the compound and maintenance media and the cell control was comprised maintenance medium alone. All cultures were incubated at 37° C. for seven days.

With 100 μg/ml of either compound either without virus or with a $10^{-1}$ concentration of poliovirus I or Coxsackie virus B5a, the culture displayed toxicity. All other cultures exposed to virus displayed cytotoxicity or infectious virus. The cell controls were normal. This data shows the compounds to inactivate less than 1% of Poliovirus I or Coxsackie B5a.

Both Poliovirus I and Coxsackie B5a virus are non-enveloped viruses. When the same tests were tried against enveloped viruses, a very different effect resulted. Following the same protocol as above, with Herpes Simplex Type II virus (G-strain) and Vero cells the data for both compounds were exactly the same. The final concentrations of the compound were 50, 100, 200 and 400 μg/ml.

At dilutions of $10^{-1}$ and $10^{-2}$ toxicity wa noticed in all cultures at any of the four dilutions of compound. At a dilution of $10^{-3}$ and using either 100, 200 or 400 μg/ml, toxicity in the cell culture was observed. All other cultures did not display viral growth or toxicity. The virus control consistently showed cytotoxicity or infectious virus in all dilutions and the cell control never showed cytotoxicity or infectious virus.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalent compounds, compositions and uses. It is to be understood that the phraseology or terminology employed herein is for the purpose of description and not of limitation. Other modifications of the above embodiments of the invention which are obvious to those skilled in the art or are within the invention's true spirit and scope are intended to be within the scope of the following claims and not within the examples given in the experiments above.

What is claimed is:

1. A compound of the formula:

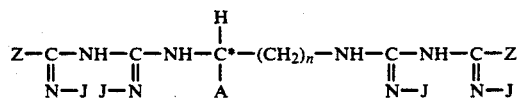

where A is a hydrogen, straight or branched chain alkane of 1-6 carbon atoms and * may be an optically active carbon where the A substituted carbon may be any of the central carbon atoms between the two guanido moieties

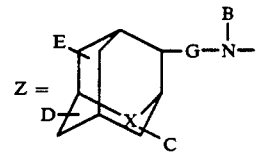

where B is hydrogen, lower alkyl, any halogen substituted lower alkyl, hydroxyalkyl, where G is zero, lower alkyl, or —NH— where C,D and E individually are hydrogen, amino, substituted amino, halogen, alkyl, lower alkyl, halogen substituted lower alkyl, amino alkyl, phenyl, phenylalkyl, haloadamantyl, pyridyl, or

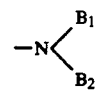

where B1 and B2 are hydrogen, lower alkyl, phenyl, phenylalkyl, COOD1, COD1, or —OD1, where D1 is hydrogen, alkyl, lower alkyl or substituted alkyl, where each J is hydrogen or halogen with any number from zero to four halogens or hydrogens being present, X is carbon, and wherein n is an integer from 2 to 30 carbon atoms wherein the polymethylene chain may be interrupted by oxygen, sulfur, nitrogen atoms and/or silicone or aromatic nuclei.

2. The compound of clam 1 wherein at least one J is a halogen.

3. A compound selected from the group consisting of the dihydrochloride or salts of:

1,5-di(N-3-methyl adamantyl-biguanido)-pentane, 1,6-di(N-3-methyl adamantyl-biguanido)-hexane,
1,8-di(N-3-methyl adamantyl biguanido)-octane,
1,6-di(N-3-methyl adamantyl biguanido)-2-methyl pentane,
1,6-di(N-adamantyl-N-chloro-biguanido)-hexane,
1,6-di(N-adamantyl)-N,N'-dichloro-biguanido)-hexane,
1,6-di(N-adamantyl-N,N',N''-trichloro-giguanido)-hexane,
1,6-di(N-adamantyl-N,N',N'',N'''-tetrachloro-biguanido)-hexane,
1,4-di(N-2-adamantyl biguanidol)-butane,
1,6-di(N-2-adamantyl-N-chloro-biguanido)-hexane,
1,6-di(N-2-adamantyl-N,N'-dichloro-biguanido)-hexane,
1,6-di(N-2-adamantyl-N,N',N''-trichloro-biguanidol-hexane,
1,6-di(N-2-adamantyl-N,N',N'',N'''-tetrachloro-giguanido)-hexane,
1,3-di(N-2-adamantyl-biguanido)-propane,
1,2-di(N-2-adamantyl-biguanido)-ethane,
1,8-di(N-2-adamantyl-biguanido)-octane,
1,9-di(N-2-adamantyl-biguanido)-nonane,
1,10-di(N-2-adamantyl-biguanido)-decane,
1,11-di(N-2-adamantyl-biguanido)-undecane,
1,12-di(N-2-adamantyl-biguanido)-dodecane,
1,13-di(N-2-adamantyl-biguanido)-tridecane and
1,6-di(N-2-adamantyl-biguanido)-2-methylpentane.

4. The compound 1,6-di(N-2-adamantyl-biguanido)-hexane dihydrochloride.

5. A method for preventing or treating a microbial infection comprising; exposing cells to the compound of claim 1 or 8 in an amount sufficient to kill or inhibit growth of the microorganism.

6. The method of claim 5 wherein J comprises at least one halogen.

7. A method for preventing or treating a microbial infection comprising; exposing cells to a compound selected from the group consisting of the dihydrochloride or salts of:
1,5-di(N-3-methyl adamantyl-biguanido)-pentane,
1,6-di(N-3-methyl adamantyl-biguanido)-hexane,
1,8-di(N-3-methyl adamantyl biguanido)-octane,
1,6-di(N-3-methyl adamantyl biguanido)-2-methyl pentane,
1,6-di(N-adamantyl-N-chloro-biguanido)-hexane,
1,6-di(N-adamantyl-N,N'-dichloro-biguanido)-hexane,
1,6-di(N-adamantyl-N,N',N''-trichlorobiguanido)-hexane,
1,6-di(N-adamantyl-N,N',N'',N'''-tetrachloro-biguanido)-hexane,
1,4-di(N-2-adamantyl biguanido)-butane,
1,6-di(N-2-adamantyl-N-chloro-biguanido)-hexane,
1,6-di(N-2-adamantyl-N,N'-dichloro-biguanido)-hexane,
1,6-di(N-2-adamantyl-N,N',N''-trichloro-biguanido)-hexane,
1,6-di(N-2-adamantyl-N,N',N'',N'''-tetrachloro-biguanido)-hexane,
1,3-di(N-2-adamantyl-biguanido)-propane,
1,2-di(N-2-adamantyl-biguanido)-ethane,
1,8-di(N-2-adamantyl-biguanido)-octane,
1,9-di(N-2-adamantyl-biguanido)-nonane,
1,10-di(N-2-adamantyl-biguanido)-decane,
1,11-di(N-2-adamantyl-biguanido)-undecane,
1,12-di(N-2-adamantyl-biguanido)j-dodecane,
1,13-di(N-2-adamantyl-biguanido)-tridecane and
1,6-di(N-2-adamantyl-biguanido)-2-methylpentane.

8. A method for preventing or treating a microbial infection comprising; exposing cells to the compound 1,6-di(N-2-adamantyl-biguanido)-hexane dihydrochloride.

9. The method of claim 5 wherein the microorganism is selected from the group consisting of gram positive bacteria, gram negative bacteria, yeasts, fungi, and enveloped viruses.

10. A composition for killing or inhibiting the growth of microorganisms comprising the compound of claim 1 or 8 and an acceptable carrier, dispersant or solid phase.

11. The composition of claim 10 wherein J comprises at least one halogen in the compound.

12. The composition of claim 10 selected from the group consisting of the dihydrochloride or salts of:
1,5-di(N-3-methyl adamantyl-biguanido)-pentane,
1,6-di(N-3-methyl adamantyl-biguanido)-hexane,
1,6-di(N-3-methyl adamantyl-biguanido)-2-methyl pentane,
1,8-di(N-3-methyl adamantyl biguanido)-octane,
1,6-di(N-adamantyl-N-chloro-biguanido)-hexane,
1,6-di(N-adamantyl-N,N'-dichloro-biguanido)-hexane,
1,6-di(N-adamantyl-N,N',N''-trichloro-biguanido)-hexane,
1,6-di(N-adamantyl-N,N',N'',N'''-tetrachloro-biguanido)-hexane,
1,4-di(N-2-adamantyl biguanido)-butane,
1,6-di(N-2-adamantyl-N-chloro-biguanido)-hexane,
1,6-di(N-2-adamantyl-N,N'-dichloro-biguanido)-hexane,
1,6-di(N-2-adamantyl-N,N',N''-trichloro-biguanido)-hexane,
1,6-di(N-2-adamantyl-N,N',N'',N'''-tetrachloro-biguanido)-hexane,
1,3-di(N-2-adamantyl-biguanido)-propane,
1,2-di(N-2-adamantyl-biguanido)-ethane,
1,8-di(N-2-adamantyl-biguanido)-octane,
1,9-di(N-2-adamantyl-biguanido)-nonane,
1,10-di(N-2-adamantyl-biguanido)-decane,
1,11-di(N-2-adamantyl-biguanido)-undecane,
1,12-di(N-2-adamantyl-biguanido)-dodecane,
1,13-di(N-2-adamantyl-biguanido)-tridecane and
1,6-di(N-2-adamantyl-biguanido)-2-methylpentane.

13. A composition for killing or inhibiting the growth of microorganisms comprising 1,6-di(N-2-adamantyl-biguanido)-hexane dihydrochloride and an acceptable carrier, dispersant or solid phase.

14. A pharmaceutical composition comprising the compound of claim 1 or 8 and a pharmaceutically acceptable carrier.

15. The pharmaceutical composition of claim 14 wherein in the compound J comprises at least one halogen.

16. The pharmaceutical composition of claim 17 wherein the compound is selected from the group consisting of the dihydrochloride or salts of:
1,5-di(N-3-methyl adamantyl-biguanido)-pentane,
1,6-di(N-3-methyl adamantyl-biguanido)-hexane,
1,3-di(N-adamantyl biguanido)-propane,
1,2-di(N-adamantyl biguanido)-ethane,
1,8-di(N-adamantyl biguanido)-octane,
1,8-di(N-3-methyl adamantyl biguanido)-octane,
1,9-di(N-adamantyl biguanido)-nonane,
1,10-di(N-adamantyl biguanido)-decane,
1,11-di(N-adamantyl biguanido)-undecane,
1,7-di(N-adamantyl biguanido)-2-methyl pentane,
1,6-di(N-3-methyl adamantyl biguanido)-2-methyl pentane, 1,12-di(N-adamantyl biguanido)-dodecane,
1,13-di(N-adamantyl biguanido)-tridecane,
1,6-di(N-adamantyl-N-chloro-biguanido)-hexane,
1,6-di(N-adamantyl-N,N'-dichloro-biguanido)-hexane,
1,6-di(N-adamantyl-N,N',N''-trichlorobiguanido)-hexane,
1,6-di(N-adamantyl-N,N',N'',N'''-tetrachlorobiguanido)-hexane,
1,14-di(N-adamantyl biguanido)-tetradecane,
1,5-di(N-adamantyl biguanido)-pentane,
1,4-di(N-2-adamantyl biguanido)-butane,
1,6-di(N-2-adamantyl-N-chlorobiguanido)-hexane,
1,6-di(N-2-adamantyl-N,N'-dichloro-biguanido)-hexane,
1,6-di(N-2-adamantyl-N,N',N''-trichloro-biguanido)-hexane,
1,6-di(N-2-adamantyl-N,N',N'',N'''-tetrachlorobiguanido)-hexane,
1,3-di(N-2-adamantyl-biguanido)-propane,
1,2-di(N-2-adamantyl-biguanido)-ethane,
1,8-di(N-2-adamantyl-biguanido)-octane,
1,9-di(N-2-adamantyl-biguanido)-nonane,
1,10-di(N-2-adamantyl-biguanido)-decane,
1,11-di(N-2-adamantyl-biguanido)-undecane,
1,12-di(N-2-adamantyl-biguanido)-dodecane,
1,13-di(N-2-adamantyl-biguanido)-tridecane and
1,6-di(N-2-adamantyl-biguanido)-2-methylpentane.

17. The pharmaceutical composition of claim 16 wherein the compound is 1,6-di(N-2-adamantyl-biguanido)-hexane dihydrochloride.

18. A compound of the formula:

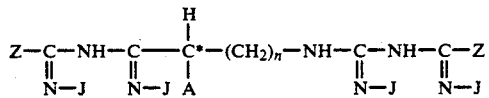

where A is a hydrogen, straight or branched chain alkane of 1–6 carbon atoms and * may be an optically active carbon
where the A substituted carbon may be any of the central carbon atoms between the two guanido moieties

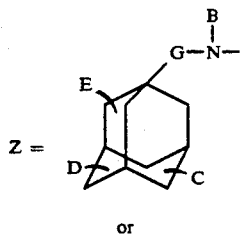

or

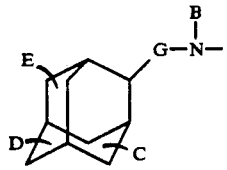

where B is hydrogen, lower alkyl, any halogen substituted lower alkyl, hydroxyalkyl,
where G is zero, lower alkyl, or —NH—
where C,D and E individually are amino, substituted amino, halogen, alkyl, lower alkyl, halogen substituted lower alkyl, amino alkyl, phenyl, phenylalkyl, haloadamantyl, pyridyl, or

where B1 and B2 are hydrogen, lower alkyl, phenyl, phenylalkyl, COOD1, COD1, or —OD1, where D1 is hydrogen, alkyl, lower alkyl or substituted alkyl,
where each J is hydrogen or halogen with any number from zero to four halogens or hydrogens being present, and wherein n is an integer from 2 to 30 carbon atoms wherein the polymethylene chain may be interrupted by oxygen, sulfur, nitrogen atoms and/or silicone or aromatic nuclei.

19. A compound of the formula:

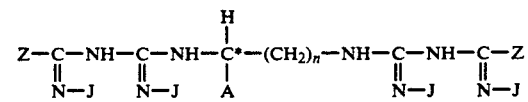

where A is a hydrogen, straight or branched chain alkane of 1–6 carbon atoms and * may be an optically active carbon
where the A substituted carbon may be any of the central carbon atoms between the two guanido moieties

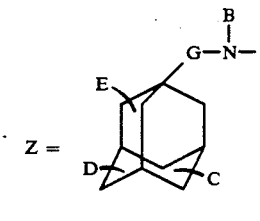

or

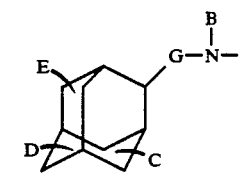

where B is hydrogen, lower alkyl, and halogen substituted lower alkyl, hydroxyalkyl,
where G is zero, lower alkyl, or —NH—
where C,D and E individually are hydrogen, amino, substituted amino, halogen, alkyl, lower alkyl, halogen substituted lower alkyl, amino alkyl phenyl, phenylalkyl, haloadamantyl, pyridyl, or

where B1 and B2 are hydrogen, lower alkyl, phenyl, phenylalkyl, COOD1, COD1, or —OD1, where D1 is hydrogen, alkyl, lower alkyl or substituted alkyl,
where each J is hydrogen or halogen with any number from one to four halogens being present, and wherein n is an integer from 2 to 30 carbon atoms wherein the polymethylene chain may be interrupted by oxygen, sulfur, nitrogen atoms and/or silicone or aromatic nuclei.

20. A compound of the formula:

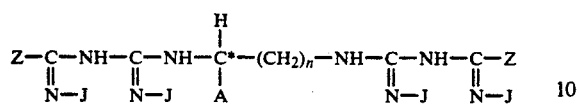

where A is a hydrogen, straight or branched chain alkane of 1-6 carbon atoms and * may be an optically active carbon where the A substituted carbon may be any of the central carbon atoms between the two guanido moieties

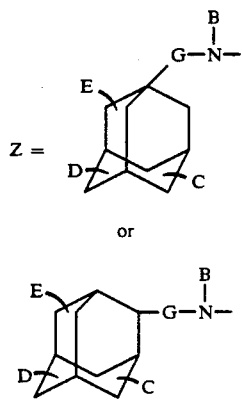

or

where B is hydrogen, lower alkyl, any halogen substituted lower alkyl, hydroxyalkyl, where G is lower alkyl, or —NH— where C,D and E individually are hydrogen, amino, substituted amino, halogen, alkyl, lower alkyl, halogen substituted lower alkyl, amino alkyl, phenyl, phenylalkyl, haloadamantyl, pyridyl, or $$-N\begin{matrix}B_1\\B_2\end{matrix}$$

where B1 and B2 are hydrogen, lower alkyl, phenyl, phenylalkyl, COOD1, COD1, or —OD1, where D1 is hydrogen, alkyl, lower alkyl or substituted alkyl, where each J is hydrogen or halogen with any number from zero to four halogens or hydrogens being present, and wherein n is an integer from 2 to 30 carbon atoms wherein the polymethylene chain may be interrupted by oxygen, sulfur, nitrogen atoms and/or silicone or aromatic nuclei.

21. A method for preventing viral growth or treat a viral infection comprising exposing cells or a sample to a compound of the formula:

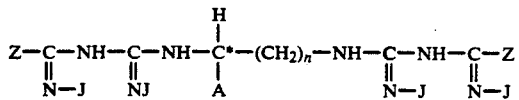

where A is a hydrogen, straight or branched chain alkane of 1-6 carbon atoms and * may be an optically active carbon where the A substituted carbon may be any of the central carbon atoms between the two guanido moieties

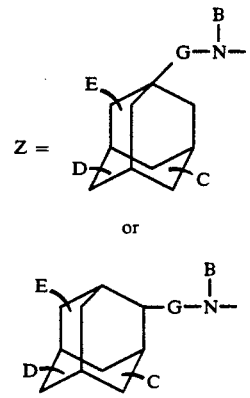

or

where B is hydrogen, lower alkyl, any halogen substituted lower alkyl, hydroxyalkyl, where G is zero, lower alkyl, or —NH— where C,D and E individually are hydrogen, amino, substituted amino, halogen, alkyl, lower alkyl, halogen substituted lower alkyl, amino alkyl, phenyl, phenylalkyl, haloadamantyl, pyridyl, or $$-N\begin{matrix}B_1\\B_2\end{matrix}$$

wehre B1 and B2 are hydrogen, lower alkyl, phenyl, phenylalkyl, COOD1, COD1, or —OD1, where D1 is hydrogen, alkyl, lower alkyl or substituted alkyl, where each J is hydrogen or halogen with any number from one to four halogens or hydrogens being present, and wherein n is an integer from 2 to 30 carbon atoms wherein the polymethylene chain may be interrupted by oxygen, sulfur, nitrogen atoms and/or silicone or aromatic nuclei.

22. The method of claim 21 wherein J comprises at least one halogen.

23. A method for preventing viral growth or treating a viral infection comprising exposing cells or a sample to a compound selected from the group consisting of the dihydrochloride or salts of:

1,5-di(N-3-methyl adamantyl-biguanido)-pentane,
1,6-di(N-3-methyl adamantyl-biguanido)-hexane,
1,3-di(N-adamantyl biguanido)-propane,
1,2-di(N-adamantyl biguanido)-ethane,
1,8-di(N-adamantyl biguanido)-octane,
1,8-di(N-3-methyl adamantyl biguanido)-octane,
1,9-di(N-adamantyl biguanido)-nonane,
1,10-di(N-adamantyl biguanido)-decane,
1,11-di(N-adamantyl biguanido)-undecane,
1,5-di(N-adamantyl biguanido)-2-methyl pentane,
1,6-di(N-3-methyl adamantyl biguanido)-2-methyl pentane,
1,12-di(N-adamantyl biguanido)-dodecane,
1,13-di(N-adamantyl biguandio)-tridecane,
1,6-di(N-adamantyl-N-chloro-biguanido)-hexane, 1,6-di(N-adamantyl-N,N'-dichloro-biguanido)-hexane,
1,6-di(N-adamantyl-N,N',N''-trichloro-biguanido)-hexane,
1,6-di(N-adamantyl-N,N',N'',N'''-tetrachloro-biguanido)-hexane,
1,14-di(N-adamantyl biguanido)-tetradecane,
1,5-di(N-adamantyl biguanido)-pentane,
1,4-di(N-2-adamantyl biguanido)-butane,
1,6-di(N-2-adamantyl-N-chloro-biguanido)-hexane,
1,6-di(N-2-adamantyl-N,N'-dichloro-biguanido)-hexane,
1,6-di(N-2-adamantyl-N,N',N''-trichloro-biguanido)-hexane,
1,6-di(N-2-adamantyl-N,N',N'',N'''-tetrachloro-biguanido)-hexane,
1,3-di(N-2-adamantyl-biguanido)-propane,
1,2-di(N-2-adamantyl-biguanido)-ethane,
1,8-di(N-2-adamantyl-biguanido)-octane,
1,9-di(N-2-adamantyl-biguanido)-nonane,
1,10-di(N-2-adamantyl-biguanido)-decane,
1,11-di(N-2-adamantyl-biguanido)-undecane,
1,12-di(N-2-adamantyl-biguanido)-dodecane,
1,13-di(N-2-adamantyl-biguanido)-tridecane and
1,6-di(N-2-adamantyl-biguanido)-2-methylpentane.

24. A method for preventing viral growth or treating a viral infection comprising exposing cells or a sample to the compound 1,6-di(N-2-adamantyl-biguanido)-hexane dihydrochloride.

25. A method for preventing viral growth or treating a viral infection comprising exposing cells or a sample to the compound 1,6-di(N-adamantyl-biguandio)-hexane dihydrochloride.

26. The method of claim 21 wherein the virus is an enveloped virus.

* * * * *